US012714120B2

(12) United States Patent
Nielsen et al.

(10) Patent No.: US 12,714,120 B2
(45) Date of Patent: Aug. 25, 2026

(54) BIOPROTECTIVE LACTIC ACID BACTERIA WITH LOW POSTACIDIFICATION

(71) Applicant: Chr. Hansen A/S, Hoersholm (DK)

(72) Inventors: Cecilie Lykke Marvig Nielsen, Hoersholm (DK); Susanne Bidstrup, Hoersholm (DK); Vera Kuzina Poulsen, Hoersholm (DK); Solvej Siedler, Hoersholm (DK); Kim Ib Soerensen, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 577 days.

(21) Appl. No.: 17/925,540

(22) PCT Filed: May 20, 2021

(86) PCT No.: PCT/EP2021/063460
§ 371 (c)(1),
(2) Date: Nov. 15, 2022

(87) PCT Pub. No.: WO2021/239574
PCT Pub. Date: Dec. 2, 2021

(65) Prior Publication Data

US 2023/0189831 A1 Jun. 22, 2023

(30) Foreign Application Priority Data

May 29, 2020 (EP) .................................... 20177382

(51) Int. Cl.
*A23C 9/123* (2006.01)
*C12N 1/20* (2006.01)
*C12R 1/225* (2006.01)

(52) U.S. Cl.
CPC .............. *A23C 9/1234* (2013.01); *C12N 1/20* (2013.01); *C12R 2001/225* (2021.05)

(58) Field of Classification Search
None
See application file for complete search history.

(56) References Cited

U.S. PATENT DOCUMENTS 11,178,884 B2 11/2021 Nielsen et al.
2014/0023749 A1* 1/2014 Jimenez .............. A23C 9/1234 435/252.9

(Continued)

FOREIGN PATENT DOCUMENTS

CN 101328470 A 12/2008
CN 103999935 A 8/2014

(Continued)

OTHER PUBLICATIONS

Leyva Salas, Marcia, et al.; "Antifungal Activity of Lactic Acid Bacteria Combinations in Dairy Mimicking Models and Their Potential as Bioprotective Cultures in Pilot Scale Applications"; Frontiers in Microbiology, vol. 9; Aug. 7, 2018; 18 pages.

(Continued)

*Primary Examiner* — Felicia C Turner
(74) *Attorney, Agent, or Firm* — Yoshimi D. Barron

(57) ABSTRACT

The present invention is in the field of dairy technology. It relates to methods for producing fermented milk products, characterized the bacterium *Lactobacillus rhamnosus* DSM 33515 or mutants obtainable therefrom is used. *Lactobacillus rhamnosus* bacteria DSM 33515 has low post-acidification in fermented milk products and can provide antimicrobial effects. The invention also provides *Lactobacillus rhamnosus* DSM 33515 or mutants obtainable therefrom as well as related compositions.

6 Claims, 3 Drawing Sheets

(56) References Cited

U.S. PATENT DOCUMENTS

| | | | |
|---|---|---|---|
| 2018/0235249 | A1 | 8/2018 | Nielsen et al. |
| 2018/0249727 | A1 | 9/2018 | Nielsen et al. |
| 2022/0151252 | A1 | 5/2022 | Nielsen et al. |

FOREIGN PATENT DOCUMENTS

| | | | | | |
|---|---|---|---|---|---|
| CN | 106591163 | A | | 4/2017 | |
| WO | WO-2012136832 | A1 | * | 10/2012 | ........... A23C 9/1234 |
| WO | 2017037046 | A1 | | 3/2017 | |
| WO | WO-2019081577 | A1 | * | 5/2019 | ........... A23C 9/1234 |

OTHER PUBLICATIONS

Zhang et al., 2019, Biotechnology Letters, 41, 633-639.

* cited by examiner

BIOPROTECTIVE LACTIC ACID BACTERIA WITH LOW POSTACIDIFICATION

CROSS-REFERENCE TO RELATED APPLICATIONS

The present application is the U.S. National Stage of International Application No. PCT/EP2021/063460, filed May 20, 2021, and claims priority to European Patent Application No. 20177382.7, filed May 29, 2020.

FIELD OF THE INVENTION

The present invention relates to *Lactobacillus rhamnosus* bacteria which reduces post-acidification in fermented milk products and can provide antimicrobial effects. Post-acidification and microbial contamination are effects frequently observed in fermented milk products stored above refrigeration temperature. The invention further provides starter cultures comprising the bacteria, methods of producing a fermented milk product using the bacteria or the cultures and the fermented milk products thus obtained, including food, feed and pharmaceutical products.

BACKGROUND OF THE INVENTION

Lactic acid bacteria (LAB) have been used over decades for increasing the shelf life of food products. During fermentation, lactic acid and other organic compounds are produced by the lactic acid bacteria, thereby reducing the pH of the food product and consequently making it unfavorable to the growth of undesired microorganisms, such as yeast and mold.

Bioprotection is defined as the extension of shelf life and enhanced safety of foods using natural or controlled antimicrobial compounds. In dairy products, spoilage by mold and yeast cells is one of the major problems negatively affecting shelf life. In the past decade, considerable efforts have been invested to explore the bioprotective potential of LAB, to identify new strains with bioprotective properties from various food sources, as well as to elucidate the mechanisms behind the observed bioactivity. Numerous metabolites produced by LAB have been identified as having antifungal activities.

Further studies have identified that competitive exclusion of a limited resource by different organisms is a major mechanism of fungal growth inhibition by Lactic acid bacteria. In particular, the depletion of the essential trace element manganese is a major bioprotective mechanism of lactic acid bacteria in dairy products. It was also shown that manganese scavenging is an active mechanism and that it requires energy to maintain a high manganese gradient (Siedler et al. "Competitive exclusion is a major bioprotective mechanism of lactobacilli against fungal spoilage in fermented milk products." *Applied and environmental microbiology* 86.7 (2020)).

At the same time, it has been found that high antifungal activity of bioprotective strains is generally accompanied by high activity, which causes post-acidification, i.e. continuation of acidification after termination of fermentation. The production of bioprotective compounds in LAB usually shows growth-associated kinetics and is therefore expected to cease if the growth is reduced (Lv et al. "Modelling the production of nisin by *Lactococcus lactis* in fed-batch culture." *Applied microbiology and biotechnology* 68.3 (2005): 322-326). Since milk acidification is typically associated with growth (Dandoy et al. "The fast milk acidifying phenotype of *Streptococcus thermophilus* can be acquired by natural transformation of the genomic island encoding the cell-envelope proteinase PrtS." *Microbial cell factories*. Vol. 10. No. S1. BioMed Central, 2011), it is expected that strains exhibiting reduced post-acidification will also have reduced bioprotective effects.

European Patent EP16182341B1 discloses a *Lactobacillus rhamnosus* strain CBS141584 having antimicrobial effects. However, no low post-acidification was mentioned.

Therefore, the development of new bioprotective strains that provide a combination of low post-acidification and high bioprotective effects is considered to be challenging.

SUMMARY OF THE INVENTION

The present invention therefore provides a bacterium of the species *Lactobacillus rhamnosus* deposited as DSM 33515 or a mutant *Lactobacillus rhamnosus* obtainable from the deposited bacteria.

The deposited bacteria or the mutant obtainable therefrom is able to (a) increase the pH of a fermented milk product comprising the deposited bacteria or the mutant during storage after fermentation in comparison to a milk product comprising *Lactobacillus rhamnosus* bacteria deposited as DSM 32092, wherein the increase in pH is at least by a value of 0.1, and wherein the increase in pH is determined after storing a product fermented with a starter culture and the *Lactobacillus rhamnosus* strain in a concentration of at least $10^7$ CFU/g over 28 days at 25° C.; and (b) decrease the growth of molds of a fermented milk product comprising the deposited bacteria or the mutant during storage after fermentation in comparison to a milk product not comprising the deposited bacteria or the mutant, wherein the decrease in the growth of molds is determined after storing a product fermented with a starter culture and said mutant in a concentration of at least $10^7$ CFU/g over 28 days at 7° C.

In a further embodiment the invention provides a bacterium of the species *Lactobacillus rhamnosus* deposited as DSM 33515 or a mutant *Lactobacillus rhamnosus* obtainable from the deposited bacteria, wherein the deposited bacteria or the mutant increases the pH of a fermented milk product comprising the deposited bacteria or the mutant during storage after fermentation in comparison to a milk product comprising *Lactobacillus rhamnosus* bacteria deposited as DSM 32092, wherein the increase in pH is at least by a value of 0.1, and wherein the increase in pH is determined after storing a product fermented with a starter culture and the *Lactobacillus rhamnosus* strain in a concentration of at least $10^7$ CFU/g over 28 days at 25° C.

In a further aspect the invention provides a bacterium of the species *Lactobacillus rhamnosus* deposited as DSM 33515 or a mutant *Lactobacillus rhamnosus* obtainable from the deposited bacteria, wherein the deposited bacteria and the mutant decrease the growth of molds in a fermented milk product comprising the deposited bacteria or the mutant during storage after fermentation in comparison to a milk product not comprising the deposited bacteria or the mutant, wherein the decrease in the growth of molds is determined after storing a product fermented with a starter culture and the deposited bacteria or the mutant in a concentration of at least $10^7$ CFU/g over 28 days at 7° C.

The invention additionally provides a composition comprising bacteria of the species *Lactobacillus rhamnosus* as described above. In one embodiment, the composition further comprises a starter culture. In another embodiment, the composition further comprises at least one cryoprotective compound. In a preferred embodiment, the composition is frozen or freeze-dried.

The invention further provides a method of producing a fermented milk product comprising adding bacteria of the species *Lactobacillus rhamnosus* strain as described above or a composition comprising the same to milk or to a milk product and fermenting the mixture at a temperature between about 22° C. and about 43° C. until a pH of 4.6 or less than 4.6 is reached.

The invention provides a fermented milk product comprising bacteria of the species *Lactobacillus rhamnosus* as described above. Preferably, the fermented milk product is obtained by the method as mentioned above. In a further embodiment, the fermented milk product maintains a pH above 3.8 when stored for at least 28 days at 25° C. In another embodiment, the bacteria of the species *Lactobacillus rhamnosus* are present in a concentration of at least $10^7$ CFU/g.

In addition, the invention provides food, feed or pharmaceutical product comprising the bacteria of the species *Lactobacillus rhamnosus* as described above or a composition comprising the same. In a preferred embodiment, the food, feed or pharmaceutical product is obtainable by the method as mentioned above.

DETAILED DESCRIPTION OF THE INVENTION

Figure 1:
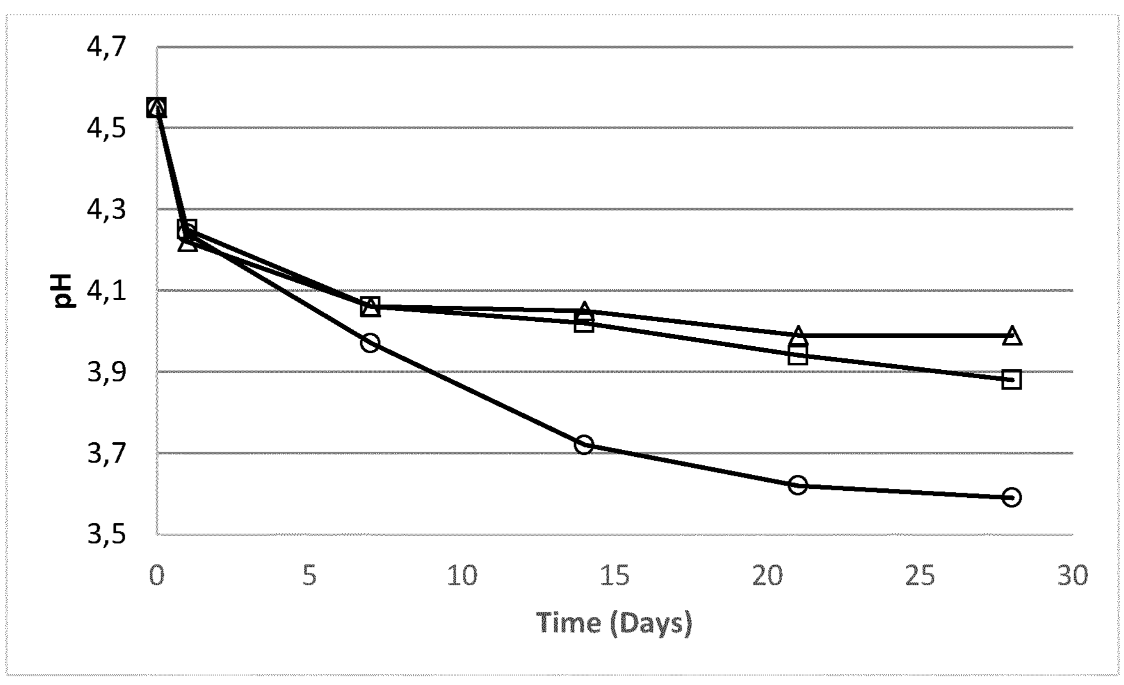
FIG. 1 shows the pH development in fermented milk products over time when stored at 25±1° C. for 28 days. The products were fermented with starter culture only (FD-DVS YF-L812, containing *Lactobacillus delbrueckii* subsp. *bulgaricus* and *Streptococcus thermophilus*) (Reference; Δ) or with starter culture in combination with bacteria deposited as DSM 33515 (□) or with starter culture in combination with bacteria deposited as DSM 32092 (○).

Food cultures with bioprotective effects offering a safe add on solution for traditionally fermented products are available, including the *Lactobacillus rhamnosus* culture DSM 32092. These bioprotective strains are used in combination with normal starter cultures to co-ferment milk to a fermented product. During the fermentation, DSM 32092 will exert the bioprotective effects and thus provide an extended shelf-life of the fermented products against molds and yeasts. Fermentation of many dairy products, such as yoghurt, are stopped and the product is cooled down at a specific pH, after fermentation the bacteria are frequently still active during storage. Further lactate is thus produced and the process is known as post-acidification. The resulting lower pH of the final product has a negative sensory impact on the product and is therefore undesirable. The invention described herein includes the development of a new and improved bioprotective strain that exhibits a combination of reduced post-acidification and high bioprotective effects. Extensive screening of over 11,000 mutants of DSM 32092 led to the identification of strain DSM 33515. This strain provides low post-acidification and high anti-fungal activity.

The *Lactobacillus rhamnosus* strain of the present invention, i.e. the strain deposited as DSM 33515 and mutants maintaining the advantageous properties, is thus characterized in that a fermented milk product comprising said strain maintains a pH above 3.8 when stored for at least 28 days at 25° C., wherein the fermented milk product is obtained by a method comprising adding said *Lactobacillus rhamnosus* strain or composition comprising the same as mentioned above to milk or to a milk product and fermenting the mixture at a temperature between about 22° C. and about 43° C. until a pH of 4.6 or less than 4.6 is reached, shaking the fermented product and cooling. It should be understood that the feature specifying that the *Lactobacillus rhamnosus* strain of present invention can maintain the pH above 3.8 when stored for at least 28 days at 25° C. merely characterizes the assay generally used to determine the effect. It is not necessary or required that the *Lactobacillus rhamnosus* strain of present invention, a composition comprising the same, including food or feed products, are in fact stored under these conditions.

The *Lactobacillus rhamnosus* strain of the present invention was generated as follows:

Ethyl methanesulfonate (EMS) mutagenesis was used to obtain a mutant pool from the mother strain DSM 32092. Pre-experiments were carried to establish efficacy and killing rate of EMS for this strain. A killing rate of ≥95% was targeted. Based on this, 15 μl EMS was added to 1 ml overnight culture ($OD_{620}$ approx. 3-4). The cultures were then incubated for 4 h at 37° C. and then diluted into series ranging from $10^{-2}$ to $10^{-6}$. Subsequently, the diluted cultures were spread on MRS plates to test for cell count. The mutant pool was spread on MRS-Difco agar using sterile glass beads and incubated for 2 days at 37° C. anaerobically. Approx. 11,000 single colonies were picked using colony picking robot, then inoculated in 96 low-well microtiter plates in 200 μl MRS-Difco broth and incubated anaerobically overnight at 37° C. A volume of 20 μl was used for milk acidification, and the remaining volume was enriched with glycerol (20%), frozen and stored. A volume of 20 μl was transferred to 96 deep-well plates containing 1980 μl UHT skim milk (1% inoculum) enriched with 2% sucrose and pH color indicator, and incubated at 40° C. for 40 h. UHT skim milk was prepared by reconstituting skim milk powder containing 38% protein, 53% lactose, <1.25 fat, and 3.9% moisture (Arla Foods amba, Denmark) to a level of dry matter of 9.5% and pasteurized at 99° C. for 30 min, followed by cooling to 40° C. The plates containing acidified milk were scanned at the bottom using color-of-pH method as described in Poulsen et al. 2019 (Poulsen, V. K., Derkx, P., Oregaard, G. (2019): "High-Throughput Screening for Texturing *Lactococcus* Strains". FEMS Microbiological Letters), where color (hue) values were converted to pH values. 462 mutant strains with good growth in MRS-Difco broth and higher end pH compared to the mother strain were collected in five 96-well micro-titer plates and used to acidify milk in the presence or absence of the starter culture YF-L812 (*Lactobacillus delbrueckii* subsp. *bulgaricus* and *Streptococcus thermophilus*). The inoculated pH color indicator milk samples were incubated on top of flat-bed scanners (HP ScanJet G4010) with temperature-controlled hoods set at 40° C. for 20 h when the starter culture was present, or 40 h in the absence of the starter culture. The 462 fermented milk samples plus controls (milk non-inoculated with any strain and the mother strain DSM 32092) were assessed for their ability to inhibit a yeast strain from the species *Debaryomyces hansenii*, which had been previously isolated as a spoilage strain from yogurt. 150 μl of the fermented milk were transferred to individual wells in a 96-well plate and the wells were inoculated with about 20 cells of the *D. hansenii* strain. After 4 days of incubation at 17° C., a dilution row was spotted on selective YGC agar plates to analyze the yeast growth by optical inspection. Leads with enhanced end pH compared to the mother strain (at least 0.2 units), which were able to inhibit *D. hansenii* at least as well as the mother strain, were subjected to three rounds of single-colony purification, and subsequently characterized for their milk acidification properties and their yeast inhibition ability in baby bottles (200-ml scale). Interestingly, the vast majority of non-post-acidifying leads lost their ability to inhibit the yeast. Only approx. 1% of the 462 leads retained their bioactivity, i.e. having bioactivity similar to the mother strain while not post-acidifying. From which DSM 33515 was selected, as it is the best performing strain with very good sensorial properties.

The *Lactobacillus rhamnosus* strain of present invention has particular advantages as it reduces the risk of post-acidification while maintaining the antifungal activity, thus improves the storage stability of food products made with these bacteria, in particular the storage stability under conditions above refrigeration temperatures.

The increase in pH caused by the mutant compared to the strain *Lactobacillus rhamnosus* bacteria deposited as DSM 32092 reaches a value of at least 0.1. The increase is determined after storing the fermented product over 28 days at 25° C.

In the context of present application, the term "lactic acid bacteria" or "LAB" is used to refer to food-grade bacteria producing lactic acid as the major metabolic end-product of carbohydrate fermentation. These bacteria are related by their common metabolic and physiological characteristics and are usually Gram-positive, low-GC, acid tolerant, non-sporulating, non-respiring, rod-shaped bacilli or cocci. During the fermentation stage, the consumption of lactose by these bacteria causes the formation of lactic acid, reducing the pH and leading to the formation of a protein coagulum. These bacteria are thus responsible for the acidification of milk and for the texture of dairy product. As used herein, the term "lactic acid bacteria" encompasses, but is not limited to, bacteria belonging to the genus of *Lactobacillus* spp., *Bifidobacterium* spp., *Streptococcus* spp., *Lactococcus* spp., such as *Lactobacillus delbrueckii* subsp. *bulgaricus, Streptococcus thermophilus, Lactobacillus lactis, Bifidobacterium animalis, Lactococcus lactis, Lactobacillus paracasei, Lactobacillus plantarum, Lactobacillus helveticus, Lactobacillus acidophilus, Bifidobacterium breve* and *Leuconostoc* spp.

A "mold" is a fungus that grows in the form of multicellular filaments called hyphae. The term "inhibit" in relation to molds refers to a decrease in the growth or sporulation or a reduction in the number or in the concentration of molds, for example in food products and/or on the surface of food products comprising the bacteria of the present invention in relation to food products which do not comprise such bacteria. The extent of inhibition provided by the *Lactobacillus rhamnosus* strain of present invention is preferably determined by growth on agar solidified fermented milk in the presence and absence of *Lactobacillus rhamnosus* bacteria. Examples of molds are member of the genus *Penicillium*, such as *Penicillium solitum, Penicillium brevicompactum, Penicillium crustosum, Penicillium roqueforti, Penicillium paneum* and *Penicillium carneum.*

Yeasts are fungi growing as single cells. The *Lactobacillus rhamnosus* strain of the present invention, i.e. the strain deposited as DSM 33515 and mutants maintaining the advantageous properties inhibit growth of molds and can further inhibit growth of yeasts. In relation to the growth of yeasts the term "inhibit" also refers to a decrease in the growth or a reduction in the number or in the concentration of yeasts, for example in food products and/or on the surface of food products comprising the bacteria of the present invention in relation to food products which do not comprise such bacteria. Again, the extent of inhibition provided by the *Lactobacillus rhamnosus* strain of present invention is preferably determined by growth on agar solidified fermented milk in the presence and absence of *Lactobacillus rhamnosus* bacteria.

The assay for determining a decrease of the growth of molds or yeasts in a fermented milk product is preferably carried out by inoculating milk with a starter culture alone as well as with a starter culture and a *Lactobacillus rhamnosus* of the present invention in a concentration of at least $10^7$ CFU/g, fermenting the milk until a pH of 4.6 is reached, mixing the fermented milk with agar, filling the mixture into agar plates, adding target mold and/or yeast contaminants in a concentration of 500 spores/spot, storing the plates for 28 days at 7° C. and comparing the growth of the mold and/or yeast on the plates containing the *Lactobacillus rhamnosus* of the present invention to the plates only containing the commercial starter culture. Full details of a respective assay are provided in Example 2.

In the present context, the term "mutant" should be understood as a strain derived from a strain of the invention, for example by means of e.g. genetic engineering, radiation and/or chemical treatment. It is preferred that the mutant is a functionally equivalent mutant, e.g. a mutant that has substantially the same, or improved, properties in particular in relation to the effects on inhibiting post-acidification and/or bioprotection, as the deposited strain. Respective mutants represent embodiments of the present invention. The term "mutant" in particular refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less than 5%, or less than 1% or even less than 0.1% of the nucleotides in the bacterial genome have been shifted with another nucleotide, or deleted, compared to the mother strain.

The use of the terms "a" and "an" and "the" and similar referents in the context of describing the invention (especially in the context of the following claims) are to be constructed to cover both the singular and the plural, unless otherwise indicated herein or clearly contradicted by context.

Respective compositions may comprise numerous further bacteria including LABs. A preferred composition of the present invention is therefore characterized in that the composition further comprises at least one further bacterium selected from one or more of the following genera and species *Lactobacillus* spp., *Bifidobacterium* spp., *Streptococcus* spp., *Lactococcus* spp., such as *Lactobacillus delbrueckii* subsp. *bulgaricus, Streptococcus thermophilus, Lactobacillus lactis, Bifidobacterium animalis, Lactococcus lactis, Lactobacillus paracasei, Lactobacillus plantarum, Lactobacillus helveticus, Lactobacillus acidophilus, Bifidobacterium breve* and *Leuconostoc* spp.

In a particularly preferred embodiment, the compositions of the present invention comprise bacteria of the species *Lactobacillus rhamnosus* deposited as DSM 33515 or a mutant *Lactobacillus rhamnosus* obtainable from the deposited bacteria and one or more further bacteria. In one embodiment, several different strains of the *Lactobacillus rhamnosus* bacteria are combined.

The composition of the present invention may additionally comprise cryoprotectants, lyoprotectants, antioxidants, nutrients, fillers, flavorants or mixtures thereof. The composition may be in frozen or freeze-dried form. The composition preferably comprises one or more of cryoprotectants, lyoprotectants, antioxidants and/or nutrients, more preferably cryoprotectants, lyoprotectants and/or antioxidants and most preferably cryoprotectants or lyoprotectants, or both. Use of protectants such as croprotectants and lyoprotectant are known to a skilled person in the art. Suitable cryoprotectants or lyoprotectants include mono-, di-, tri- and polysaccharides (such as glucose, mannose, xylose, lactose, sucrose, trehalose, raffinose, maltodextrin, starch and gum arabic (acacia) and the like), polyols (such as erythritol, glycerol, inositol, mannitol, sorbitol, threitol, xylitol and the like), amino acids (such as proline, glutamic acid), complex substances (such as skim milk, peptones, gelatin, yeast extract) and inorganic compounds (such as sodium tripolyphosphate). Suitable antioxidants include ascorbic acid, citric acid and salts thereof, gallates, cysteine, sorbitol, mannitol, maltose. Suitable nutrients include sugars, amino acids, fatty acids, minerals, trace elements, vitamins (such as vitamin B-family, vitamin C). The composition may optionally comprise further substances including fillers (such as lactose, maltodextrin) and/or flavorants.

LAB are most commonly added to milk in the form of a starter culture. The term "starter" or "starter culture" as used in the present context refers to a culture of one or more food-grade microorganisms, in particular to lactic acid bacteria, which are responsible for the acidification of the milk base. Starter cultures may be fresh but are most frequently frozen or freeze-dried. These products are also known as "Direct Vat Set" (DVS) cultures and are produced for direct inoculation of a fermentation vessel or vat for the production of a dairy product, such as a fermented milk product or a cheese. Respective starter cultures are commercially available from numerous sources and include Premium 5.0, YF-L812, F-DBA YoFlex Mild 2.0, F-DVS YF-L901, FD-DVS CH-1, four cultures commercially available from Chr. Hansen containing mixtures of *Streptococcus thermophilus* and *Lactobacillus delbrueckii* subsp. *bulgaricus.*

In one aspect the present invention therefore provides compositions in the form of a solid frozen or freeze-dried starter culture comprising lactic acid bacteria in a concentration of at least $10^9$ colony forming units (CFU) per g of frozen material or in a concentration of at least $10^{10}$ CFU/g of frozen material or in a concentration of at least $10^{11}$ CFU/g of frozen material. These starter cultures further comprise bacteria of the species *Lactobacillus rhamnosus* deposited as DSM 33515 or a mutant *Lactobacillus rhamnosus* obtainable from the deposited bacteria.

There is also described a *Lactobacillus rhamnosus* strain, wherein the bacterium is characterized in that it increases the pH of a fermented milk product comprising the *Lactobacillus rhamnosus* strain during storage after fermentation in comparison to a milk product fermented with the same starter culture containing the *Lactobacillus rhamnosus* bacteria deposited as DSM 32092, wherein the increase in pH is at least by a value of 0.1, and wherein the increase in pH is determined after storing a product fermented with a starter culture and the *Lactobacillus rhamnosus* in a concentration of at least $10^7$ CFU/g over 28 days at 25° C.

In a further embodiment the present invention provides methods of producing a fermented milk product which comprises adding said *Lactobacillus rhamnosus* strain of the present invention or the composition comprising the same to milk or to a milk product and fermenting the mixture at a temperature between about 22° C. and about 43° C. until a pH of 4.6 or less than 4.6 is reached.

In the context of the present application, the term "milk" is broadly used in its common meaning to refer to liquids produced by the mammary glands of animals or by plants. In accordance with the present invention the milk may have been processed and the term "milk" includes whole milk, skim milk, fat-free milk, low fat milk, full fat milk, lactose-reduced milk, or concentrated milk. Fat-free milk is non-fat or skim, milk product. Low-fat milk is typically defined as milk that contains from about 1% to about 2% fat. Full fat milk often contains 2% fat or more. The term "milk" is intended to encompass milks from different mammal and plant sources. Mammal sources of milk include, but are not limited to cow, sheep, goat, buffalo, camel, lama, mare and deer. Plant sources of milk include, but are not limited to, milk extracted from soybean, pea, peanut, barley, rice, oat, quinoa, almond, cashew, coconut, hazelnut, hemp, sesame seed and sunflower seed. In the methods and products of the present invention, milk derived from cows is most preferably used as a starting material for the fermentation.

The term "milk" also includes fat-reduced and/or lactose-reduced milk products. Respective products can be prepared using methods well known in the art and are commercially available. Lactose-reduced milk can be produced according to any method known in the art, including hydrolyzing the lactose by lactase enzyme to glucose and galactose, or by nanofiltration, electrodialysis, ion exchange chromatograph and centrifugation.

The term "milk product" or "milk base" is broadly used in the present application to refer to a composition based on milk or milk components which can be used as a medium for growth and fermentation of LAB. The milk product or base comprises components derived from milk and any other component that can be used for the purpose of growing or fermenting LAB.

Prior to fermentation, the milk substrate may be homogenized and pasteurized according to methods known in the art. "Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices. "Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

The present invention further provides methods of, wherein the fermented product is stored at a temperature above 7° C., preferably at a temperature between 7° C. and 25° C. The product may be stored at any time but is preferably stored for a period of at least 14 days and wherein the pH of the fermented milk product is maintained above pH 4.0 during storage.

The invention further provides methods of producing a food, feed or pharmaceutical product comprising a method of producing a fermented milk product as described above and the food, feed or pharmaceutical product obtainable by this method.

Fermentation is carried out to produce food products, feed products or pharmaceuticals. The terms "fermented milk product", "food" or "feed" product refer to products obtainable by the fermentation methods of the present invention and include cheese, yoghurt, fruit yoghurt, yoghurt beverage, strained yoghurt (Greek yoghurt, Labneh), quark, fromage frais and cream cheese. The term food further encompasses other fermented food products, including fermented meat, such as fermented sausages, and fermented fish products.

The term "cheese" is understood to encompass any cheese, including hard, semi-hard and soft cheeses, such as cheeses of the following types: Cottage, Feta, Cheddar, Parmesan, Mozzarella, Emmentaler, Danbo, Gouda, Edam, Feta-type, blue cheeses, brine cheeses, Camembert and Brie. The person skilled in the art knows how to convert the coagulum into cheese, methods can be found in the literature, see e.g. Kosikowski, F. V., and V. V. Mistry, "Cheese and Fermented Milk Foods", 1997, 3rd Ed. F. V. Kosikowski, L. L. C. Westport, CT As used herein, a cheese which has a NaCl concentration below 1.7% (w/w) is referred to as a "low-salt cheese".

In the context of the present application, the term "yoghurt" refers to products comprising *Streptococcus thermophilus* and *Lactobacillus delbrueckii* subsp. *bulgaricus* and optionally other microorganisms such as *Lactobacillus delbrueckii* subsp. *lactis, Bifidobacterium animalis* subsp. *lactis, Lactococcus lactis, Lactobacillus acidophilus* and *Lactobacillus paracasei*, or any microorganism derived therefrom. The lactic acid strains other than *Streptococcus thermophilus* and *Lactobacillus delbrueckii* subsp. *bulgaricus*, are included to give the finished product various properties, such as the property of promoting the equilibrium of the flora. As used herein, the term "yoghurt" encompasses set yoghurt, stirred yoghurt, drinking yoghurt, Petit Suisse, heat treated yoghurt, strained or Greek style yoghurt characterized by a high protein level and yoghurt-like products.

In particular, term "yoghurt" encompasses, but is not limited to, yoghurt as defined according to French and European regulations, e.g. coagulated dairy products obtained by lactic acid fermentation by means of specific thermophilic lactic acid bacteria only (i.e. *Lactobacillus delbrueckii* subsp. *bulgaricus* and *Streptococcus thermophilus*) which are cultured simultaneously and are found to be live in the final product in an amount of at least 10 million CFU (colony-forming unit)/g. Yoghurts may optionally contain added dairy raw materials (e.g. cream) or other ingredients such as sugar or sweetening agents, one or more flavoring(s), fruit, cereals, or nutritional substances, especially vitamins, minerals and fibers, as well as stabilizers and thickeners. Optionally the yoghurt meets the specifications for fermented milks and yoghurts of the AFNOR NF 04-600 standard and/or the codex StanA-IIa-1975 standard. In order to satisfy the AFNOR NF 04-600 standard, the product must not have been heated after fermentation and the dairy raw materials must represent a minimum of 70% (m/m) of the finished product.

Deposits and Expert Solution

The applicant requests that a sample of the deposited microorganisms stated below may only be made available to an expert, subject to available provisions governed by Industrial Property Offices of States Party to the Budapest Treaty, until the date on which the patent is granted.

The applicant deposited the *Lactobacillus rhamnosus* strain DSM 32092 on 2013 Jun. 5 at German Collection of Microorganisms and Cell Cultures (Deutsche Sammlung von Mikroorganismen und Zellkulturen GmbH; DSMZ), Inhoffenstr. 7B, D-38124 Braunschweig and received the accession No.: DSM 32092.

The applicant deposited the *Penicillium solitum* DSM 32093 on 2015 Jul. 16 at German Collection of Microorganisms and Cell Cultures (Deutsche Sammlung von Mikroorganismen und Zellkulturen GmbH; DSMZ), Inhoffenstr. 7B, D-38124 Braunschweig and received the accession No.: DSM 32093.

The applicant deposited the *Penicillium brevicompactum* DSM 32094 on 2015 Jul. 16 at German Collection of Microorganisms and Cell Cultures (Deutsche Sammlung von Mikroorganismen und Zellkulturen GmbH; DSMZ), Inhoffenstr. 7B, D-38124 Braunschweig and received the accession No.: DSM 32094.

The applicant deposited the *Lactobacillus rhamnosus* DSM 33515 on 2020 May 5 at German Collection of Microorganisms and Cell Cultures (Deutsche Sammlung von Mikroorganismen und Zellkulturen GmbH; DSMZ), Inhoffenstr. 7B, D-38124 Braunschweig and received the accession No.: DSM 33515.

The applicant deposited the *Penicillium crustosum* DSM 33517 on 2020 May 5 at German Collection of Microorganisms and Cell Cultures (Deutsche Sammlung von Mikroorganismen und Zellkulturen GmbH; DSMZ), Inhoffenstr. 7B, D-38124 Braunschweig and received the accession No.: DSM 33517.

The applicant deposited the *Penicillium* roqueforti DSM 33518 on 2020 May 5 at German Collection of Microorganisms and Cell Cultures (Deutsche Sammlung von Mikroorganismen und Zellkulturen GmbH; DSMZ), Inhoffenstr. 7B, D-38124 Braunschweig and received the accession No.: DSM 33518.

The applicant deposited the *Penicillium* paneum DSM 33519 on 2020 May 5 at German Collection of Microorganisms and Cell Cultures (Deutsche Sammlung von Mikroorganismen und Zellkulturen GmbH; DSMZ), Inhoffenstr. 7B, D-38124 Braunschweig and received the accession No.: DSM 33519.

The applicant deposited the *Penicillium carneum* DSM 33520 on 2020 May 5 at German Collection of Microorganisms and Cell Cultures (Deutsche Sammlung von Mikroorganismen und Zellkulturen GmbH; DSMZ), Inhoffenstr. 7B, D-38124 Braunschweig and received the accession No.: DSM 33520.

EXAMPLES

Example 1

Bioprotective *Lactobacillus rhamnosus* Strain Deposited as DSM 33515—Low Impact on Post-Acidification Strain *Lactobacillus rhamnosus* deposited as DSM 33515 was tested for impact on post-acidification in comparison to starter culture alone and the mother strain deposited as DSM 32092.

For that purpose, a homogenized milk base consisting of 2.8% protein, 1.2% fat and 10% sucrose was heat-treated at 95±1° C. for 5 min and cooled immediately. A commercial starter culture (FD-DVS YF-L812 or FD-DVS Premium 5.0) was inoculated at 0.02% (v/w), and the inoculated milk was distributed into 3 liter buckets. One bucket was inoculated with *Lactobacillus rhamnosus* bacteria deposited as DSM 33515 in total concentration of $1\times10^7$ CFU/g, one bucket was inoculated with the *Lactobacillus rhamnosus* bacteria deposited as DSM 32092 in total concentration of $1\times10^7$ CFU/g, and one bucket was used as a reference and was only inoculated with the starter culture. All bottles were incubated in a water bath at 43±1° C. and fermented at these conditions until pH of 4.60±0.1 was reached. After fermentation, the bottles were vigorously stirred to break the coagulum, dispensed into 50 ml cups and immediately cooled on ice.

To monitor the effect on post acidification, the three fermented milk samples (starter-only, starter+bacteria deposited as DSM 33515 and starter+DSM 32092) were stored at 7±1° C., 12±1° C. and 25±1° C. for 28 days as well as 37±1° C. for 7 days, and pH was measured on day 1, 7, 14, 21 and 28.

Figure 2:
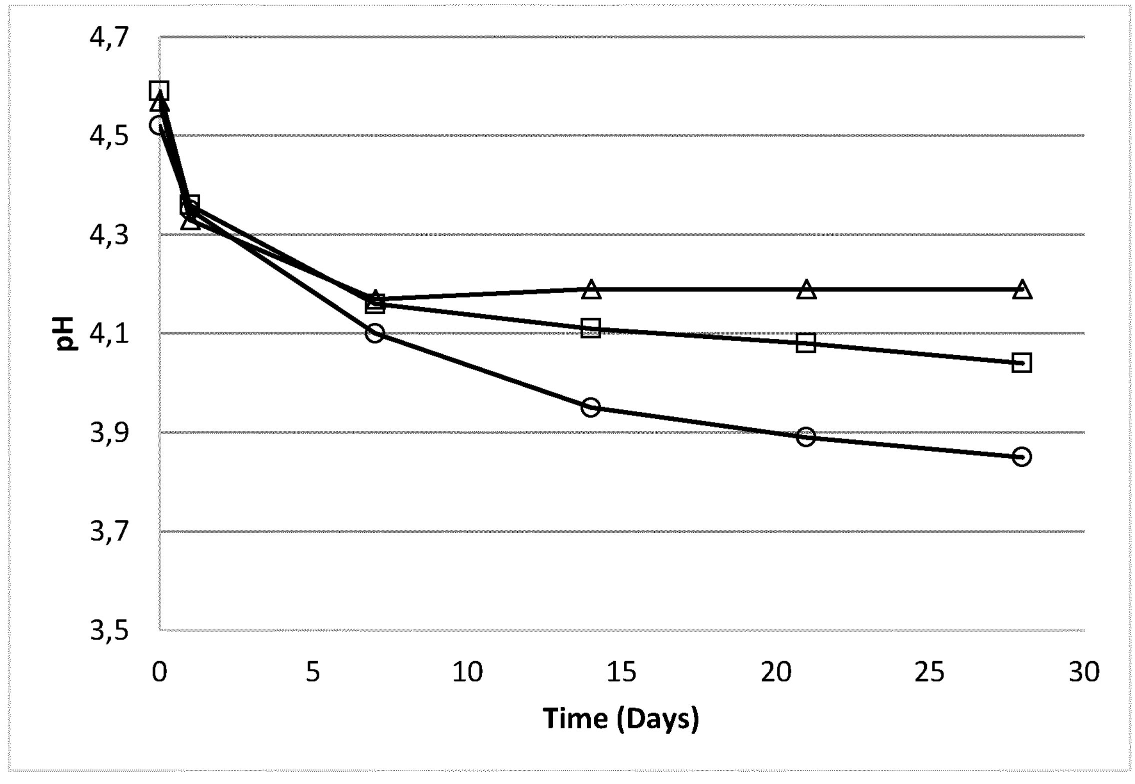
FIG. 2 shows the pH development in fermented milk products over time when stored at 25±1° C. for 28 days. The products were fermented with starter culture only (FD-DVS Premium 5.0, containing *Lactobacillus delbrueckii* subsp. *bulgaricus* and *Streptococcus thermophilus*) (Reference, Δ) or with starter culture in combination with bacteria deposited as DSM 33515 (□) or with starter culture in combination with bacteria deposited as DSM 32092 (○).

The effect on post-acidification when combined with FD-DVS YF-L812 and FD-DVS Premium 5.0 is illustrated in FIG. 1 and FIG. 2 respectively, showing that addition of *Lactobacillus rhamnosus* bacteria deposited as DSM 33515 induced less post-acidification compared to *Lactobacillus rhamnosus* bacteria deposited as DSM 32092.

Example 2

*Lactobacillus rhamnosus* Strain DSM 33515 Combines Low Effect on Post-Acidification with High Anti-Mold Effect For the analysis of the inhibitory effect of *Lactobacillus rhamnosus* bacteria deposited as DSM 33515 a semi-quantitative agar-assay was used, resembling the manufacturing process and product of yoghurt:

A homogenized milk base consisting of 2.8% protein, 1.2% fat and 10% sucrose was heat-treated at 95±1° C. for 5 min and cooled immediately. A commercial starter culture (FD-DVS YF-L812) was inoculated at 0.02% (v/w), and the inoculated milk was distributed into 3 L buckets. One bucket was inoculated with *Lactobacillus rhamnosus* bacteria deposited as DSM 33515 in total concentration of $1\times10^7$ CFU/g, another bucket was inoculated with *Lactobacillus rhamnosus* DSM 32092 in total concentration of $1\times10^7$ CFU/g, and one bucket was used as a reference and only inoculated with the starter culture. All buckets were incubated in a water bath at 43±1° C. and fermented at these conditions until pH of 4.60±0.1 was reached. After fermentation, the buckets were vigorously stirred to break the coagulum, dispensed into 200 ml cups and immediately cooled in a cooling chamber. Then the fermented milk was warmed to a temperature of 40° C. and added 40 ml of a 5% sterile agar solution that had been melted and cooled down to 60° C. This solution of fermented milk and agar was then poured into sterile Petri dishes and the plates were dried in a LAF bench for 30 min.

Spore suspension of the following six different molds were spotted in concentration of 500 spores/spot onto the agar plates: *P. brevicompactum* deposited as DSM 32094, *P. crustosum* deposited as DSM 33517, *P. solitum* deposited as DSM 32093, *P. carneum* deposited as DSM 33520, *P. paneum* deposited as DSM 33519 and *P. roqueforti* deposited as DSM 33518. Three molds were spotted on each plate and the target contaminants were added in concentrations of 500 spores/spot. Plates were incubated at 7±1° C. for 28 days and regularly examined for the growth of molds.

Figure 3:
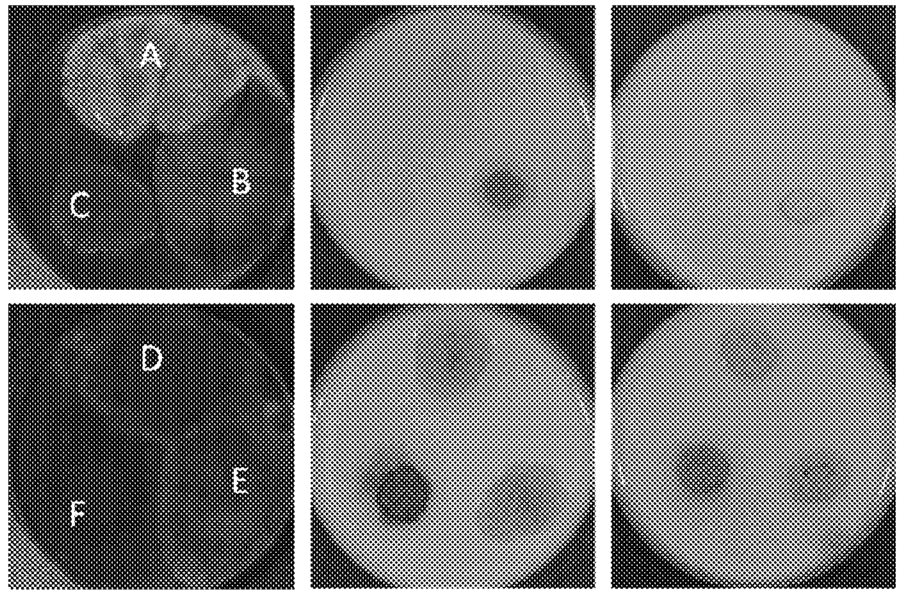
FIG. 3 shows the growth of molds on plates prepared from milk fermented with a starter culture alone (reference, first column), or with a starter culture in combination with *Lactobacillus rhamnosus* bacteria deposited as DSM 33515 (second column) or with a starter culture in combination with *Lactobacillus rhamnosus* bacteria deposited as DSM 32092 (third column). The target contaminants were added in concentrations of 500 spores/spot: (A) *P. brevicmpactum*, (B) *P. crustosum*, (C) *P. solitum*, (D) *P. carneum*, (E) *P. paneum* and (F) *P. roqueforti*. The plates were incubated at 7±1° C. for 28 days.

Results of the agar-assay are presented in FIG. 3, showing that all of the tested molds grew very well on the agar plates made from milk fermented only with the starter culture (reference). However, when *Lactobacillus rhamnosus* bacteria deposited as DSM 33515 was present during milk fermentation the resulting plates inhibited growth of the six *Penicillium* species tested. The effect of *Lactobacillus rhamnosus* was at levels similar to *Lactobacillus rhamnosus* DSM 32092, which is known to induce more post-acidification.

Example 3

Sensory Evaluation

The bioprotective *Lactobacillus rhamnosus* strain deposited as DSM 33515 was in fermented dairy products stored at slightly accelerated temperatures (12° C.) or at 25° C. for two weeks tested for impact on sensory compared to starter culture alone and the mother strain DSM 32092.

A homogenized milk base consisting of 2.8% protein, 1.2% fat and 10% sucrose was heat-treated at 95±1° C. for 5 min and cooled immediately. A commercial starter culture (FD-DVS YF-L812) was inoculated at 0.02% (v/w), and the inoculated milk was distributed into 3 L buckets. One bucket was inoculated with *Lactobacillus rhamnosus* bacteria deposited as DSM 33515 in a total concentration of $1\times10^7$ CFU/g, one bucket was inoculated with *Lactobacillus rhamnosus* bacteria deposited as DSM 32092 in total concentration of $1\times10^7$ CFU/g, and one bucket was used as a reference and only inoculated with the starter culture. All buckets were incubated in a water bath at 43±1° C. and fermented at these conditions until pH of 4.60±0.1 was reached. After fermentation, the buckets were vigorously stirred to break the coagulum, dispensed into 200 mL cups and immediately cooled in a cooling chamber. One set of samples was stored at 12° C. for two weeks and another set of samples was stored at 25° C. for two weeks.

In a Descriptive Analysis, a trained panel rates specified attributes of a product on scales of perceived intensity. These quantitative ratings were then used to describe the similarities and differences between the products of the evaluated product set (Lawless, H. T., & Heymann, H. (2010). Sensory evaluation of food: principles and practices. Springer Science & Business Media):

Twelve trained judges participated in the test to evaluate six samples with only three of relevance here. The attribute list was based on the evaluation of the same samples stored at either 25° C. For the evaluation, the samples were presented to the judges in randomized order following a Latin square design in two replicates i.e. 12 samples in total. Attribute intensities were rated on a structured line scale with five compartments that was labeled with "none" on the left end and "a lot" on the right.

Statistical evaluation of the results for the intensity evaluation included three-way MANOVA (multivariate analysis of variance) with Wilks test to check overall sample differences and ANOVA (Analysis of variance) to find for which attribute there were significant differences, both considering the factors product, judge and replicate as well as their two-way interactions. The Least Significant Difference (LSD) test was used to detect significant differences among the product samples when the attributes had a significant product effect. A significance level of $\alpha$=0.05 was selected for the study.

Results of the sensory evaluations performed on samples stored for 14 days at 12° C. and 25° C. are presented in Table 1 and Table 2, respectively. These results show that addition of *Lactobacillus rhamnosus* bacteria deposited as DSM 33515 together with the starter culture has improved the sensory properties of the product when stored at 12° C. or 25° C. for 14 days compared to the mother strain DSM 3351. Specifically, samples with DSM 32092 was perceived with less buttery aroma compared to the reference in samples stored at 12° C. for 14 days. When samples were stored at 25° C. for 14 days the *Lactobacillus rhamnosus* DSM 32092 gave more sourness, but less sweet taste and milky aroma compared to the samples inoculated with the starter culture alone.

TABLE 1

Results of the sensory evaluations performed on samples stored at 12° C. for 14 days. Attribute list, F-values for the factor product from the three-way ANOVA for the samples with the corresponding p-value and significance for each attribute, Mean values and grouping of the samples based on the least significant difference test (LSD) for the attributes that were found to be significantly different among the products, different letters indicate significant differences at $p < 0.05$.

| | F-value | | Mean values (grouping) | | |
|---|---|---|---|---|---|
| Attribute | for product | p-value | Reference | DSM 33515 | DSM 32092 |
| Yoghurt flavor | 0.03 | 1 | 54.20 A | 53.67 A | 54.22 A |
| Milky | 1.19 | 0.329 | 52.28 A | 51.65 A | 44.57 A |
| Buttery | 2.17 | 0.072 | 42.32 A | 31.03 AB | 29.92 B |
| Yeast | 1 | 0.426 | 36.02 A | 25.93 A | 28.20 A |
| Cardboard | 1.08 | 0.384 | 6.39 A | 7.84 A | 7.79 A |
| Astringency | 0.23 | 0.948 | 25.3 A | 27.9 A | 30.7 A |
| Sweet | 1.86 | 0.118 | 47.22 AB | 45.63 AB | 37.65 B |
| Sour | 1.32 | 0.27 | 38.27 AB | 43.25 AB | 42.69 AB |
| Bitter | 0.47 | 0.797 | 6.96 A | 5.05 A | 5.97 A |
| Off-flavor | 1.23 | 0.31 | 5.54 A | 4.43 A | 5.67 A |

*significant at $p < 0.05$

TABLE 2

Results of the sensory evaluations performed on samples stored at 25° C. for 14 days. Attribute list, F-values for the factor product from the three-way ANOVA for the samples with the corresponding p-value and significance for each attribute, Mean values and grouping of the samples based on the least significant difference test (LSD) for the attributes that were found to be significantly different among the products, different letters indicate significant differences at $p < 0.05$.

| | F-value | | Mean values (grouping) | | |
|---|---|---|---|---|---|
| Attribute | for product | p-value | Reference | DSM 33515 | DSM 32092 |
| Yoghurt flavor | 0.49 | 0.779 | 62.31 A | 56.59 A | 60.13 A |
| Milky | 3.38 | 0.01* | 54.64 A | 52.09 A | 34.57 C |
| Buttery | 1.71 | 0.15 | 42.15 A | 39.37 A | 31.71 AB |
| Yeast | 2.66 | 0.033* | 31.13 ABC | 22.55 C | 27.03 BC |
| Cardboard | 1.25 | 0.3 | 6.84 B | 11.35 A | 8.98 AB |
| Astringency | 1.54 | 0.195 | 24.7 B | 31.3 AB | 27.9 AB |
| Sweet | 7.33 | <0.001* | 57.18 A | 45.03 AB | 21.25 C |
| Sour | 7.15 | <0.001* | 43.84 C | 49.68 BC | 78.87 A |
| Bitter | 1.17 | 0.337 | 7.47 AB | 14.84 A | 8.72 AB |
| Off-flavor | 0.89 | 0.498 | 3.38 A | 13.86 A | 9.34 A |

*significant at $p < 0.05$

It can be seen from the table that samples prepared with DSM 33515 were perceived to be more milky, sweeter and less sour than the samples prepared with DSM 32092.

Example 4

*Lactobacillus rhamnosus* Strain DSM 33515 Shows Less Impact on Post-Acidification Compared to CBS141584

*Lactobacillus rhamnosus* DSM 33515 was tested for impact on post-acidification in comparison to starter culture alone and strain deposited as CBS141584 disclosed in European Patent EP16182341.

For that purpose, a homogenized milk base consisting of 2.8% protein, 1.2% fat and 10% sucrose was heat-treated at 95±1° C. for 5 min and cooled immediately. A commercial starter culture (FD-DVS YF-L812, Chr. Hansen A/S Denmark, containing *Lactobacillus delbrueckii* subsp. *bulgaricus* and *Streptococcus thermophilus*) was inoculated at 0.02% (v/w), and the inoculated milk was distributed into 3 liter buckets. One bucket was inoculated with *Lactobacillus rhamnosus* bacteria deposited as DSM 33515 in total concentration of $1\times10^7$ CFU/g, one bucket was inoculated with CBS141584 in total concentration of $1\times10^7$ CFU/g, and one bucket was used as a reference and was only inoculated with the starter culture. All bottles were incubated in a water bath at 43±1° C. and fermented at these conditions until pH of 4.60±0.1 was reached. After fermentation, the bottles were vigorously stirred to break the coagulum, dispensed into 50 ml cups and immediately cooled on ice.

To monitor the effect on post acidification, the three fermented milk samples (starter-only, starter+bacteria deposited as DSM 33515 and starter+CBS141584) were stored at 7±1° C., and 25±1° C. for 28 days, and pH was measured on day 1, 7, 14, 21 and 28.

Figure 4:
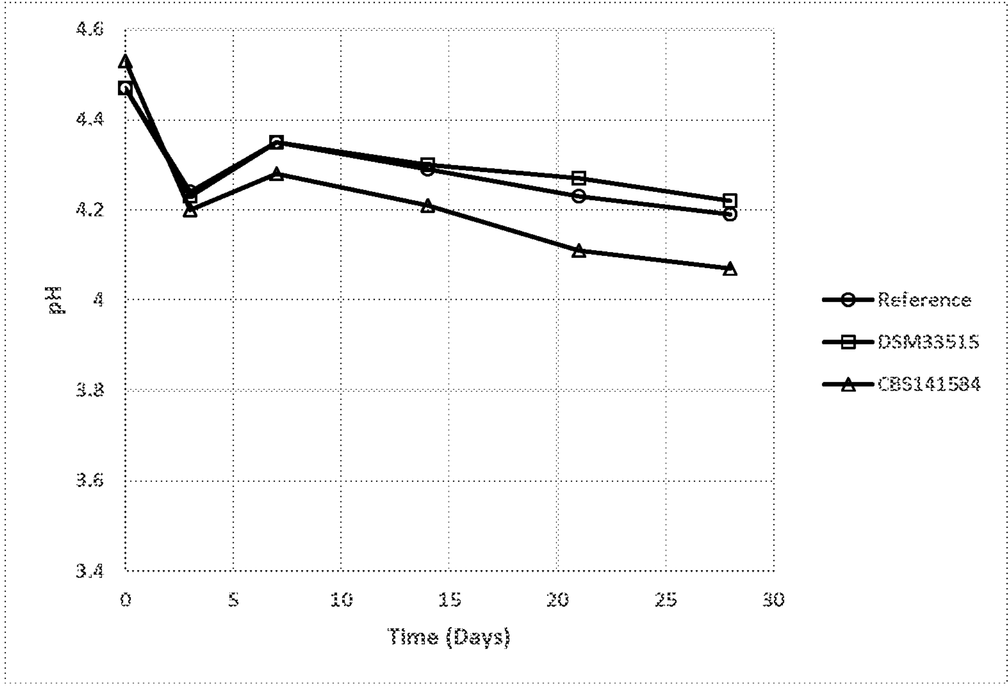
FIG. 4 shows the pH development in fermented milk products over time when stored at 7±1° C. for 28 days. The products were fermented with starter culture only (Reference, ○), or with starter culture in combination with bacteria deposited as DSM 33515 (□) or with starter culture in combination with CBS141584 (Δ).
Figure 5:
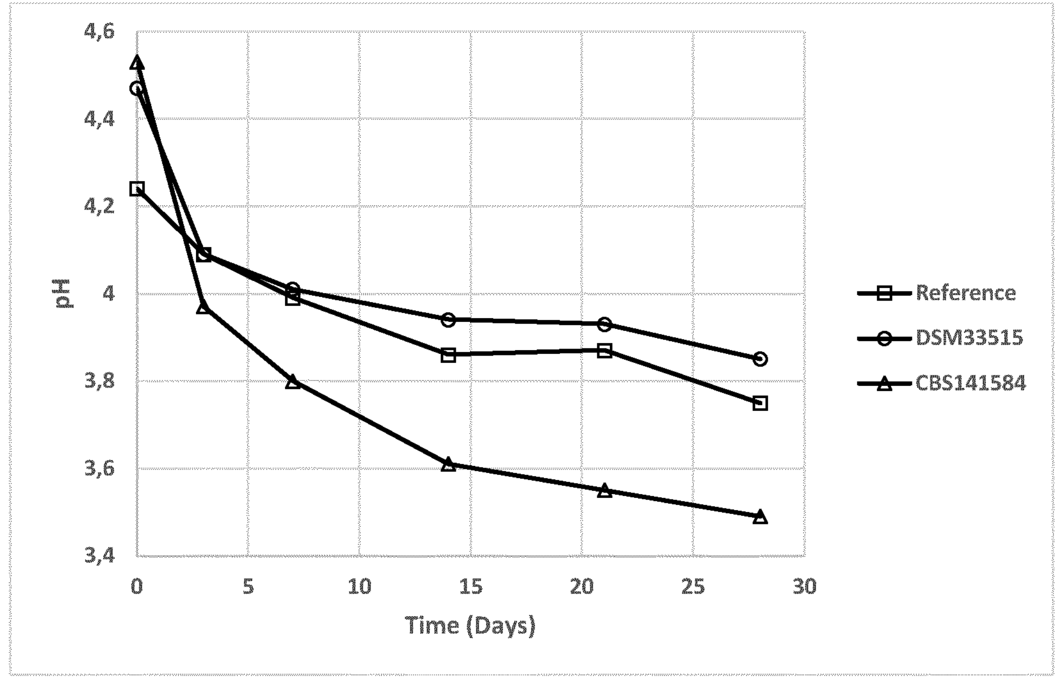
FIG. 5 shows the pH development in fermented milk products over time when stored at 25±1° C. for 28 days. The products were fermented with starter culture only (Reference, ○), or with starter culture in combination with bacteria deposited as DSM 33515 (□) or with starter culture in combination with the *Lactobacillus rhamnosus* strain CBS141584 (Δ).

FIG. 4 and FIG. 5 show the effect on post-acidification of DSM 33515 and CBS141584 when combined with the starter culture. Clearly, the addition of *Lactobacillus rhamnosus* bacteria DSM 33515 induced less post-acidification compared to CBS141584.

The invention claimed is:

1. A method of producing a fermented milk product, comprising adding a *Lactobacillus rhamnosus* strain to a milk product to obtain a mixture and fermenting the mixture at a temperature between about 22° C. and about 43° C. until a pH of 4.6 or less is reached, wherein the *Lactobacillus rhamnosus* strain is selected from:

(i) a *Lactobacillus rhamnosus* strain deposited at the Deutsche Sammlung von Mikroorganismen und Zellkulturen GmbH (Braunschweig, Germany) (DSMZ) under accession number DSM 33515 and;

(ii) a mutant strain thereof obtained from the deposited strain of part (i), wherein the *Lactobacillus rhamnosus* strain exhibits the following properties:

(a) increases the pH of a test fermented milk product by at least 0.1 during storage after fermentation as compared to a milk product comprising a *Lactobacillus rhamnosus* strain deposited at the DSMZ under accession number DSM 32092, wherein the test fermented milk product is obtained by fermenting a milk product with a starter culture and at least $10^7$ CFU/g of the *Lactobacillus rhamnosus* strain, and wherein the increase in pH is determined after storing the test fermented milk product for 28 days at 25° C.; and (b) decreases growth of molds in a test fermented milk product during storage after fermentation as compared to a milk product that does not comprise the *Lactobacillus rhamnosus* strain, wherein the test fermented milk product is obtained by fermenting a milk product with a starter culture and at least $10^7$ CFU/g of the *Lactobacillus rhamnosus* strain, wherein the decrease in growth of molds is determined after storing the test fermented milk product for 28 days at 7° C.

2. The method according to claim 1, further comprising adding a starter culture to the mixture prior to the fermenting.

3. A fermented milk product obtained by the method according to claim 1.

4. The fermented milk product according to claim 3, wherein the fermented milk product maintains a pH above 3.8 when stored for 28 days at 25° C.

5. The fermented milk product according to claim 3, comprising at least $10^7$ CFU/g of the *Lactobacillus rhamnosus* strain deposited at the Deutsche Sammlung von Mikroorganismen und Zellkulturen GmbH (Braunschweig, Germany) (DSMZ) under accession number DSM 33515.

6. A food, feed or pharmaceutical product obtained by the method of claim 1.

* * * * *